(12) United States Patent
Taff et al.

(10) Patent No.: US 9,134,233 B2
(45) Date of Patent: Sep. 15, 2015

(54) DROP DETECTION ASSEMBLY AND METHOD

(75) Inventors: Brian M. Taff, Albany, OR (US); Alexander Govyadinov, Corvallis, OR (US)

(73) Assignee: HEWLETT-PACKARD DEVELOPMENT COMPANY, L.P., Houston, TX (US)

( * ) Notice: Subject to any disclaimer, the term of this patent is extended or adjusted under 35 U.S.C. 154(b) by 0 days.

(21) Appl. No.: 14/123,194

(22) PCT Filed: May 31, 2011

(86) PCT No.: PCT/US2011/038608
§ 371 (c)(1),
(2), (4) Date: Nov. 29, 2013

(87) PCT Pub. No.: WO2012/166119
PCT Pub. Date: Dec. 6, 2012

(65) Prior Publication Data
US 2014/0098156 A1    Apr. 10, 2014

(51) Int. Cl.
  *B41J 29/393* (2006.01)
  *B41J 29/38* (2006.01)
  *G01N 21/64* (2006.01)
  *B41J 2/045* (2006.01)
  *B41J 2/125* (2006.01)

(52) U.S. Cl.
  CPC ............ *G01N 21/64* (2013.01); *B41J 2/04561* (2013.01); *B41J 2/04586* (2013.01); *B41J 2/125* (2013.01)

(58) Field of Classification Search
  CPC .... B41J 2/125; B41J 2/04561; B41J 2/04586; G01N 21/64
  USPC ............................................ 347/19, 100, 14
  See application file for complete search history.

(56) References Cited

U.S. PATENT DOCUMENTS

| 4,779,003 | A | 10/1988 | Tatsuno |
| 5,646,654 | A | 7/1997 | Widder |
| 6,576,155 | B1 * | 6/2003 | Barbera-Guillem ....... 106/31.15 |
| 6,744,046 | B2 | 6/2004 | Valaskovic et al. |
| 6,958,482 | B2 | 10/2005 | Martinez et al. |

(Continued)

FOREIGN PATENT DOCUMENTS

| JP | 2004058627 A | 2/2004 |
| KR | 20050092985 A | 9/2005 |
| WO | 2010044765 A1 | 4/2010 |

OTHER PUBLICATIONS

Particle Sciences, Inc., "Manufacture of Microspheres as Carrier Particles for Active Biomolecules," Technical Paper; printed from the Internet on Apr. 11, 2011. [Online] http://www.particlesciences.com/docs/Manufacture_of_Microspheres_as_Carrier_Particles_for_Active_Biomolecules.pdf.

(Continued)

*Primary Examiner* — Jannelle M Lebron
(74) *Attorney, Agent, or Firm* — Hanley Flight & Zimmerman, LLC

(57) ABSTRACT

A drop detection method comprises ejecting an ink drop that includes a fluorescent agent, illuminating the ink drop in flight with excitation light to excite the fluorescent agent, detecting fluorescence emitted by the drop in flight, having a longer wavelength than a wavelength of the excitation light, and, prior to such detecting, filtering out light having a shorter wavelength than the fluorescence wavelength; and a printer with drop detection assembly for performing the method.

19 Claims, 12 Drawing Sheets

(56) References Cited

U.S. PATENT DOCUMENTS

| | | | |
|---|---|---|---|
| 7,483,767 B2 | 1/2009 | Montaser et al. | |
| 8,333,453 B2 | 12/2012 | Dudenhoefer et al. | |
| 2002/0140760 A1 | 10/2002 | Bruch et al. | |
| 2002/0158938 A1 | 10/2002 | Doval | |
| 2003/0090534 A1 | 5/2003 | Valero et al. | |
| 2004/0233465 A1* | 11/2004 | Coyle et al. | 106/31.15 |
| 2006/0044341 A1 | 3/2006 | Reichelsheimer et al. | |
| 2006/0172060 A1 | 8/2006 | Teichman et al. | |
| 2006/0261295 A1 | 11/2006 | Barea | |
| 2007/0023037 A1 | 2/2007 | Larsen et al. | |
| 2007/0024658 A1 | 2/2007 | Diol et al. | |
| 2008/0018909 A1 | 1/2008 | Osaka et al. | |
| 2008/0186373 A1 | 8/2008 | Rolly | |
| 2008/0259107 A1 | 10/2008 | Farr et al. | |
| 2009/0015609 A1 | 1/2009 | Choo | |
| 2009/0086190 A1 | 4/2009 | Kodama et al. | |
| 2009/0231403 A1* | 9/2009 | Shi et al. | 347/101 |
| 2009/0244163 A1 | 10/2009 | Govyadinov | |
| 2009/0288580 A1 | 11/2009 | Cai | |
| 2010/0033519 A1 | 2/2010 | Cai et al. | |
| 2011/0109679 A1 | 5/2011 | Govyadinov et al. | |
| 2011/0121021 A1 | 5/2011 | Dudenhoefer et al. | |
| 2011/0221815 A1 | 9/2011 | Ward et al. | |

OTHER PUBLICATIONS

HPDC, International Search Report and Written Opinion dated Jun. 16, 2011, PCT App. No. PCT/US2011/038608, 9 p.

United States Patent and Trademark Office, "Office Action", issued in connection with U.S. Appl. No. 14/588,821, mailed on Apr. 1, 2015, 20 pages.

United States Patent and Trademark Office, "Notice of Allowance", issued in connection with U.S. Appl. No. 13/123,804, mailed on Mar. 17, 2015, 21 pages.

International Searching Authority, "International Preliminary Report on Patentability", issued in connection with PCT Application No. PCT/US2008/011809, Apr. 19, 2011, 5 pages.

International Searching Authority, "International Search Report", issued in connection with PCT Application No. PCT/US2008/011809, mailed on May 29, 2009, 2 pages.

International Searching Authority, "Written Opinion", issued in connection with PCT Application No. PCT/US2008/011809, mailed on May 29, 2009, 4 pages.

United States Patent and Trademark Office, "Notice of Allowance", issued in connection with U.S. Appl. No. 13/123,804, mailed on Nov. 5, 2014, 14 pages.

United States Patent and Trademark Office, "Final Office Action", issued in connection with U.S. Appl. No. 13/123,804, mailed on Jul. 18, 2014, 13 pages.

United States Patent and Trademark Office, "Office Action", issued in connection with U.S. Appl. No. 13/123,804, mailed on Mar. 31, 2014, 16 pages.

United States Patent and Trademark Office, "Final Office Action", issued in connection with U.S. Appl. No. 13/123,804, mailed on Sep. 19, 2013, 21 pages.

United States Patent and Trademark Office, "Office Action", issued in connection with U.S. Appl. No. 13/123,804, mailed on May 9, 2013, 15 pages.

United States Patent and Trademark Office, "Advisory Action", issued in connection with U.S. Appl. No. 13/123,804, mailed on Nov. 29, 2013, 3 pages.

United States Patent and Trademark Office, "Notice of Allowance," issued in connection with U.S. Appl. No. 13/123,804, mailed on Jun. 9, 2015, 18 pages.

* cited by examiner

DROP DETECTION ASSEMBLY AND METHOD

CROSS-REFERENCE TO RELATED APPLICATION

The present application is the U.S. National Stage under 35 U.S.C. §371 of International Patent Application No. PCT/US2011/038608, filed 31 May 2011, the disclosure of which is hereby incorporated herein by reference.

BACKGROUND

To achieve adequate image/print quality (IPQ), many inkjet printers require precise knowledge of the "health" or condition of each nozzle in a printhead prior to the initiation of a print job. For example, nozzles through which ink drops are ejected may become clogged or otherwise cease to operate properly. As a result, nozzle health detection or diagnostic components have become a part of many printing devices to determine whether to clean or perform other maintenance, or whether some nozzles should be inactivated and other compensatory nozzles used instead.

BRIEF DESCRIPTION OF THE DRAWINGS

For a detailed description of exemplary embodiments of the invention, reference will now be made to the accompanying drawings in which.

NOTATION AND NOMENCLATURE

Figure 1:
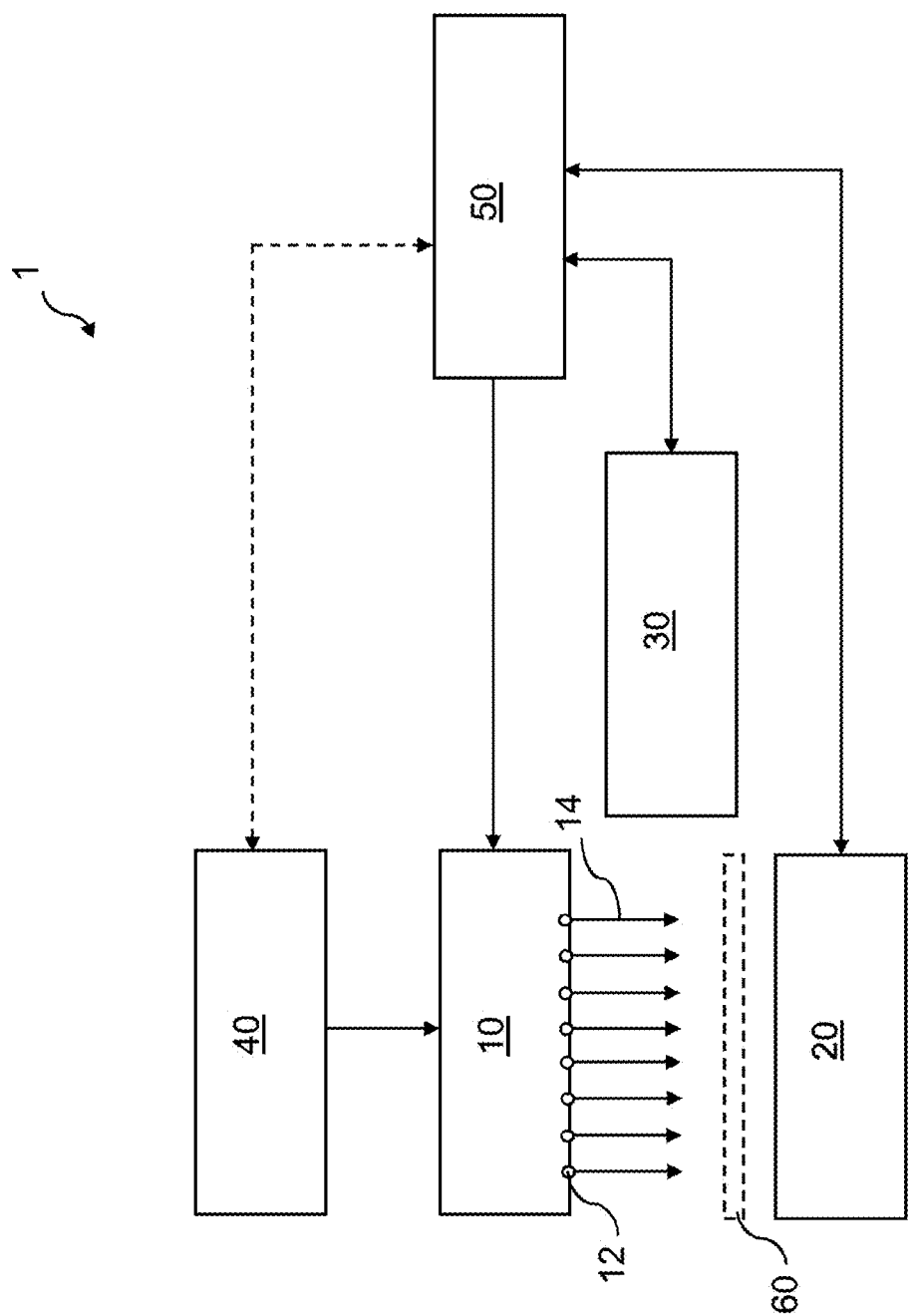
FIG. 1 is a block diagram illustrating a printer with a photoluminescence-based drop detection assembly, in accordance with some embodiments.

Certain terms are used throughout the following description and claims to refer to particular system components. Technology companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . .."

The term "about" when referring to a numerical value or range is intended to encompass the values resulting from experimental error that can occur when taking measurements. Such measurement deviations are usually within plus or minus 10 percent of the stated numerical value.

The term "black optical density" or "KOD" when referring to an inkjet printed image is the measurement of the change in reflectance $OD=\log_{10}(I_i/I_r)$, where $I_i$ and $I_r$ are incident and reflected light intensities, respectively. The higher the KOD value, the darker the black colored image obtained.

The term "image/print quality (IPQ)" or "human detectable print output quality" refers to one or more qualities of a printed image that are observable by the human eye when observed on-page. For example, visible gaps in a fill area or visible missing lines in a printed pattern may occur as a result of a missing nozzle.

The term "colorant," as used herein, refers to a pigment, dye, or a combination of both pigment and dye, capable of being dispersed or dissolved in an ink vehicle, and imparting to the ink a visible color (i.e., wavelength selective absorption and or reflection).

The terms "fluorescent agent," "fluorescent additive," "fluorophore agent," "fluorophore additive" and "dopant" refer to an ink component that is different than the colorant except where specifically indicated to the contrary, and which emits radiation or light (photoluminescence) of one or more given wavelengths as a result of absorption of excitation light at another, typically shorter, wavelength.

The terms "fluorescent signal strength" ("fluorescence signal strength") or "photoluminescent signal strength ("photoluminescence signal strength") refer to the magnitude or intensity of the measured electrically-detectable response collected by one or more in-system detectors used to assess nozzle health characteristics.

The term "in-flight" refers to ejected ink drops in transit as observed prior to their contacting either a print media or an ink collection vessel (e.g., in a service station). The print media and the ink collection vessel are sometimes referred to herein as an ink "drop receptor."

"Liquid vehicle," "ink vehicle," or simply "vehicle," as used herein, refers to the fluid medium in which colorant is dispersed or dissolved to form an ink.

As used herein the term "ink-jet printing" refers to non-contact methods for producing images through the deposition of ink droplets in a dot-by-dot on-demand manner. These scripted drop depositions deliver ink to an image-recording medium in response to appropriate operational commands (such as digital signals). Common methods for propelling ink droplets in drop-on-demand ink-jet printing include piezoelectric transduction and thermally-actuated bubble formation/expansion.

"Decap time" refers to the amount of time a printhead can be left uncapped (i.e., uncovered and exposed to an ambient atmospheric environment) and idle between instances of use and still maintain the capacity to fire properly upon resumed use. Typically, ink dries in uncapped jetting nozzles when exposed to air (due to the evaporation of volatile in-ink species), often causing nozzle clogging, drop misdirection, the reduction or augmentation of measured drop velocities, and/or other firing defects.

The term "inkjet nozzle performance" and/or "inkjet nozzle health" refers to the ability of a print nozzle to maintain a predetermined drop direction (i.e., the ability to avoid misdirecting its affiliate ink droplet stream), while also delivering fired ink droplets at specified and reproducible velocities (e.g., with velocity that does not deviate by more than ±10%). Other indicators of nozzle performance may include, but are not limited to, ink drops that are absent where they should be present, the comparative match between specified and actual numbers, sizes and/or shapes of ink drops in a given print job, and the reproducibility of drop volumes and weights (e.g., volumes or weights deviating by no more than ±10%.) A "healthy" jetting nozzle also produces drops on the page that are colored as they are intended; for example, the drops are not enriched in color, depleted in color, or missing altogether.

Temperature, ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range has been explicitly recited. For example, a weight range of about 0.1 wt. % to about 10 wt. % should be interpreted to include not only the explicitly recited concentration limits of about 0.1 wt. % to about 10 wt. %, but also to include individual concentrations such as 1 wt. %, 2 wt. %, 5 wt. %, and sub-ranges such as 0.2 wt. % to 1.5 wt. %, 0.5 wt. % to 8 wt. %, and so forth.

DETAILED DESCRIPTION

The following discussion is directed to various embodiments of the invention. The embodiments disclosed should not be interpreted or otherwise used as limiting the scope of the disclosure, including the claims. In addition, the following description has broad application, and the discussion of any embodiment is meant only to be exemplary of that embodiment, and not intended to intimate that the scope of the disclosure, including the claims, is limited to that embodiment.

Drop Detection Assembly

Figure 2:
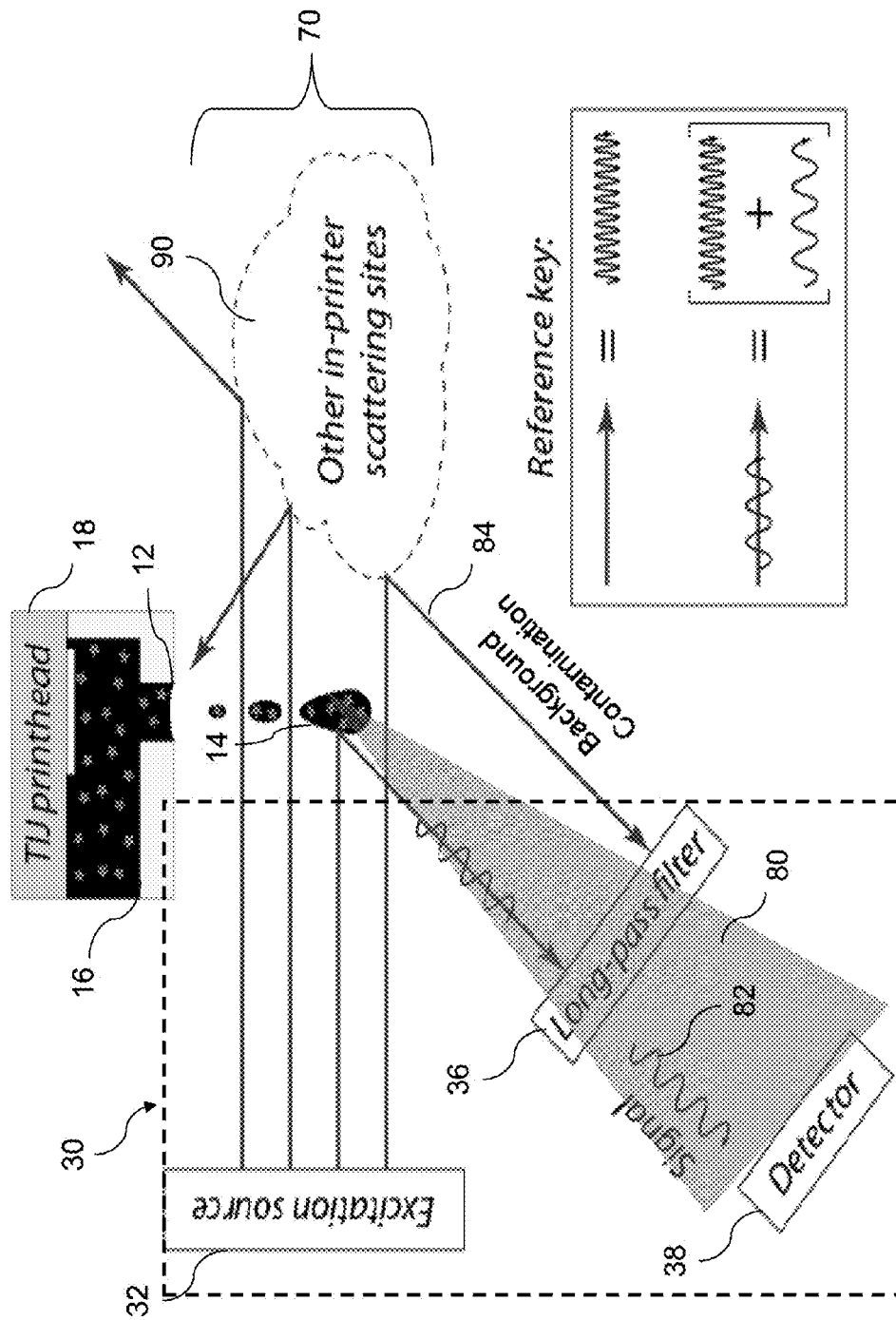
FIG. 2 illustrates a photodetector, light source and light filter as employed in the drop detection assembly of FIG. 1, in accordance with some embodiments.

FIG. 1 is a block diagram illustrating an example of an inkjet printer 1 that includes a print bar 10, a media transport mechanism (transporter) 20, a photoluminescence-based drop detector assembly 30, an ink supply 40, and an electronic printer controller 50. For example, print bar 10 may be a single print bar configured to span a print media 60, or multiple print bars that together span media 60. For convenience, print bar 10 is referred to in the singular hereinafter. In some embodiments, print bar 10 comprises an array of printhead modules, each carrying one or more printhead dies and the associated mechanical and electrical components for dispensing ink drops on to a sheet or web of paper or other print media 60 (shown in phantom lines) during operation of the printer. For example, as illustrated in FIG. 2, a typical thermal inkjet printhead die (16) in a thermal inkjet printhead (18), for example, includes an orifice plate arrayed with ink ejection orifices or nozzles 12 and firing resistors formed on an integrated circuit chip positioned behind the ink ejection orifices. The printhead die(s) in each module are electrically connected to controller 50 and are fluidically connected to ink supply 40, during use of the printer. Alternatively, a printhead may contain a piezoelectric transducer, or any other drop ejection transducer, for ejection of ink droplets 14 from an orifice or nozzle 12.

Controller 50 represents generally the programming, processor(s) and associated memories, and the electronic circuitry and components needed to control the operative elements of a printer 1. Drop detector assembly 30 is configured to optically interact with ejected in-flight drops 14 from print bar 10, during operation of printer 1, as described in more detail below.

Although for the purposes of illustration this description focuses primarily on a page wide array inkjet printer, it should be understood that a similar drop detection strategy may be employed with other printing or drop dispensing configurations. For instance, a print bar or printhead may instead be configured to move back and forth across a print media 60 dispensing ink drops 14 from one or more nozzles 12 during operation of printer 1 in printing mode. A scan-based printer may have a ink drop receiver or ink collection vessel like those known in the art located at one end of transporter 20.

FIG. 1 depicts an ink supply 40 as part of printer 1, however, in some implementations the ink supply may be initially omitted from printer 1. In that case, printer 1 may be configured to receive an ink supply which is provided separately, prior to use of the printer, and is then coupled to print bar 10 prior to operation of printer 1. Optionally, ink supply 40 may be electronically coupled to controller 50 (as indicated by dashed arrows in FIG. 1).

Figure 3A:
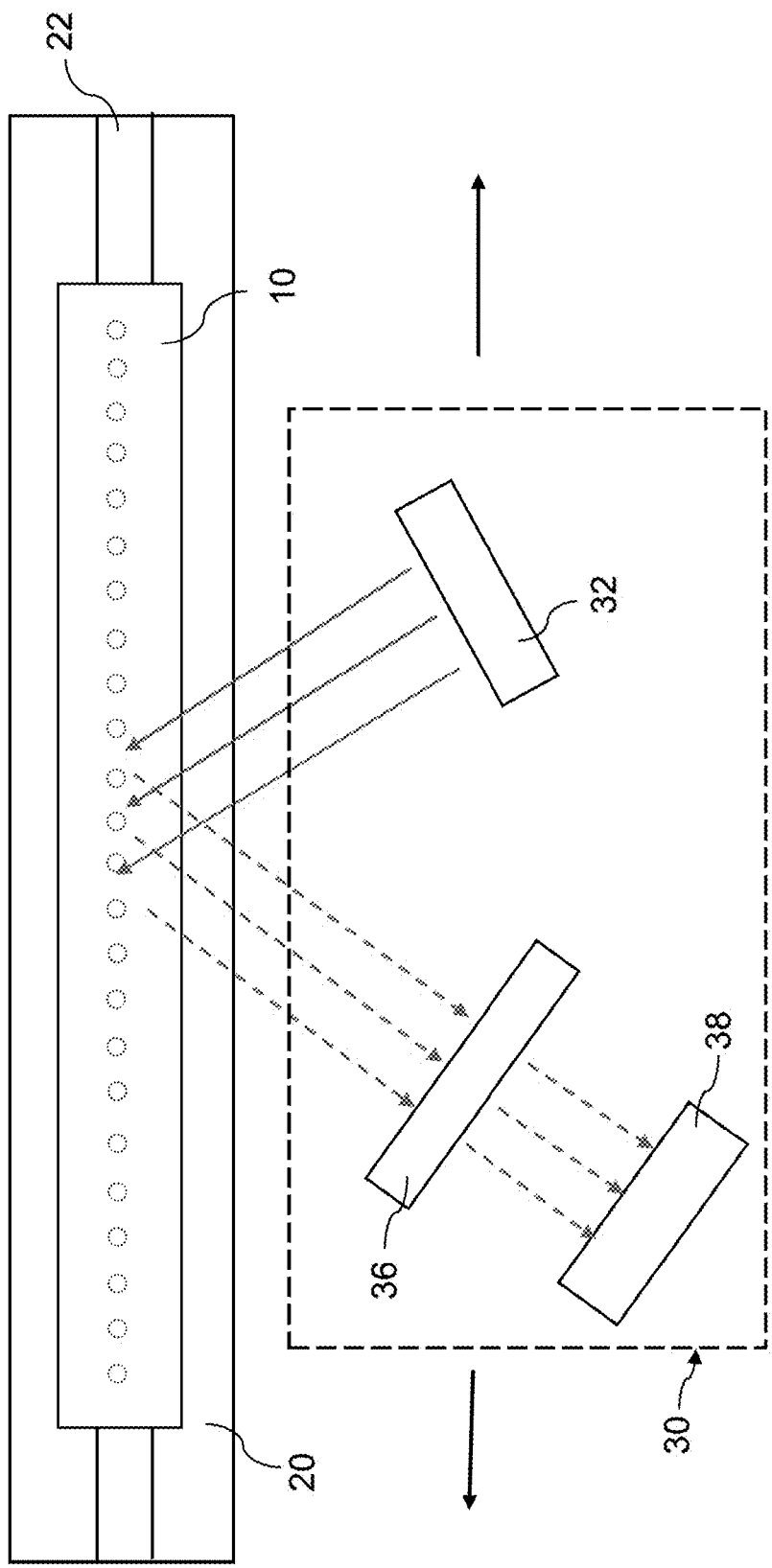
FIG. 3A is a top down view illustrating the positioning of a media transporter, print bar and drop detection assembly, in accordance with some embodiments.
Figure 3B:
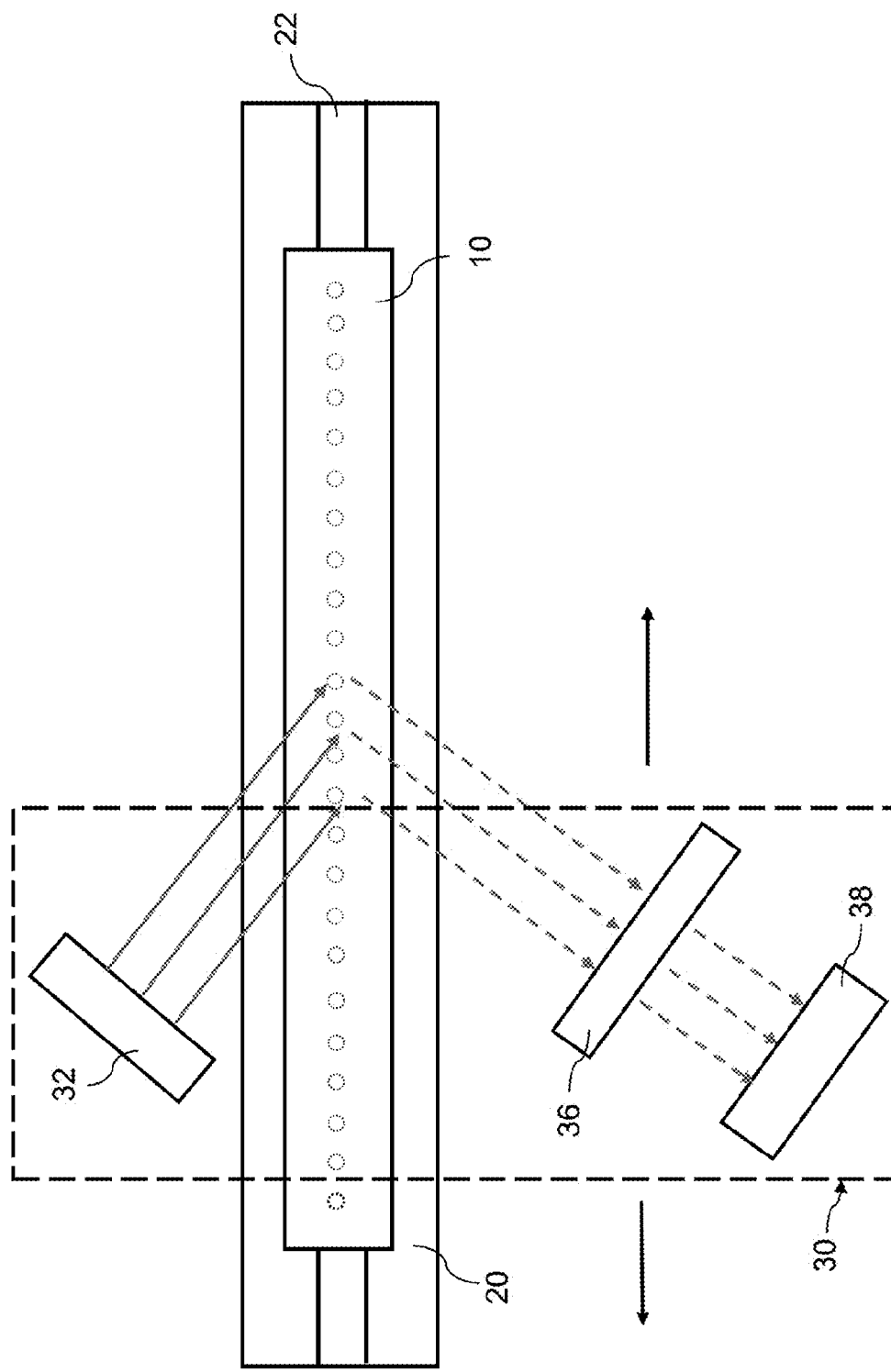
FIG. 3B is a top down view illustrating the positioning of another media transporter, print bar and drop detection assembly, in accordance with some embodiments.
Figure 3C:
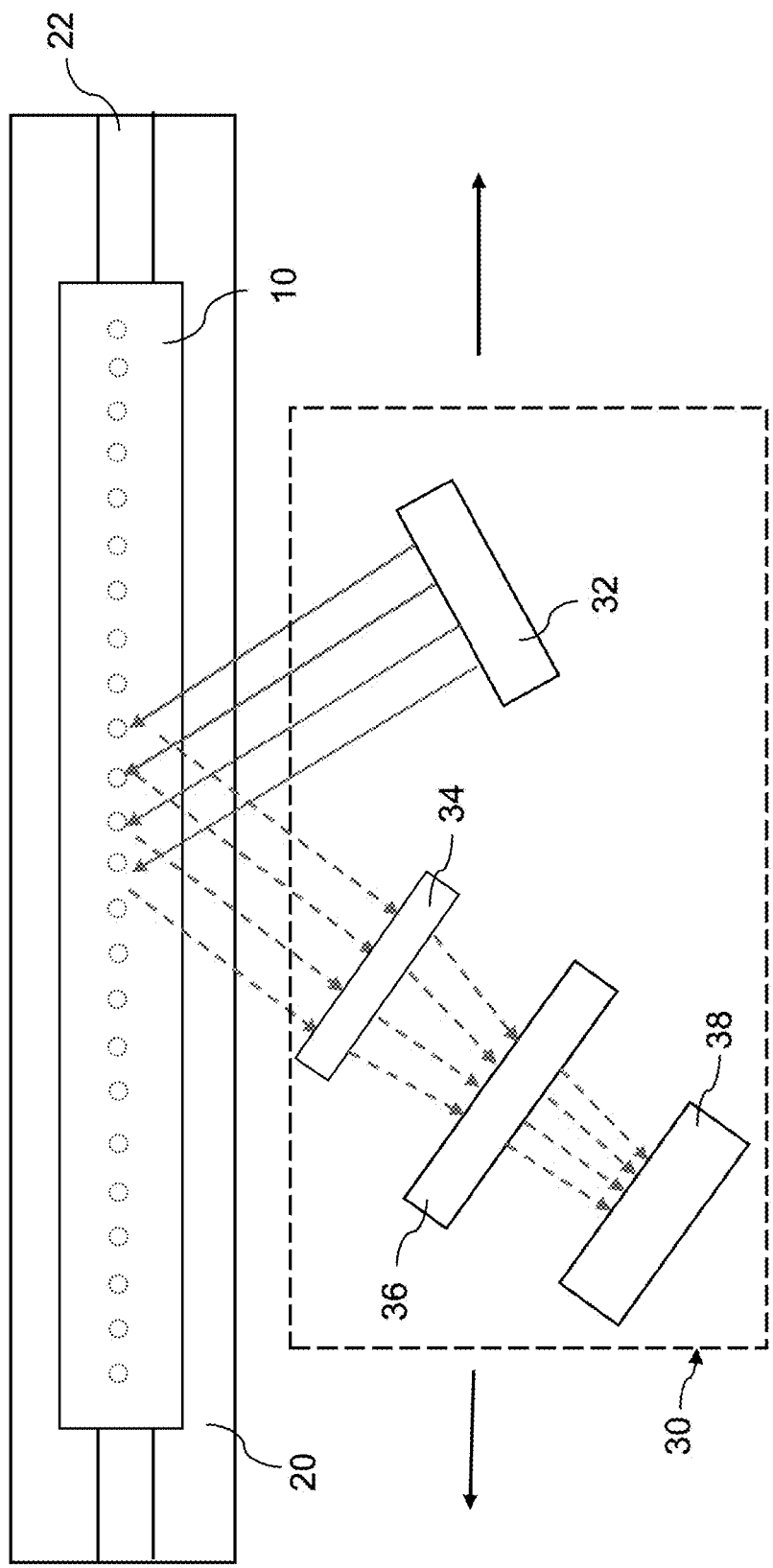
FIG. 3C is a top down view illustrating the positioning and components of another drop detection assembly, in accordance with some embodiments.

In FIG. 2, drop detector assembly 30 includes an excitation light source 32 for illuminating ink drops in flight, an optical long-wavelength passing filter 36, and a photoluminescence detector (photodetector) 38. Optical long-wavelength passing filter 36 is positioned in front of photoluminescence detector (photodetector) 38 in detection path 80, for monitoring and harvesting fluorescent emissions from in-flight drops 14 passing through drop zone 70. The length of drop zone 70 is the distance between an ink receiver and an orifice or nozzle 12 on a printhead 18. For example, as shown in FIGS. 3A-B, an ink receiver 22 may be a trough or spittoon running the width of transporter 20 in a printer configured for page wide printing. A drop detector assembly 30 may also include an imaging or non-imaging collection optic located in the detection path to help focus collected light onto photodetector 38. Various types of collection optics include, but are not limited to, a classical lens, Fresnel lens, reflector, diffraction and holographic optics. For example, as illustrated in FIG. 3C, lens 34 is positioned between filter 36 and drop 14. Excitation light source 32 may be either fixed or movable. The light source is any source of collimated light beam suitable for illuminating ink drops in flight. For example, an edge emitting laser (EEL), vertical cavity surface emitting laser (VCSEL) or a light emitting diode (LED). The light emitted by an LED source may be collimated by a lens to produce a narrow, substantially parallel beam. Suitable excitation light sources are commercially available from such suppliers as Edmond Optics and Thorlabs, for example.

Optical filter 36 is selected to provide a sharp cutoff between its pass and non-pass regions, and the pass region provides high transparency. For example, a filter with 90% or better transmissivity in the pass band, a sharp (i.e., less than 40 nm) cutoff transition zone, and OD ratings of 5 or better is used in some cases. The filter 36 is selected to pass a narrow or broad band of the fluorescence wavelength emitted by the fluorescent agent, and to exclude or block background wavelengths shorter than or equal to the wavelength of the excitation light. As another example, the optical filter may be tuned to suppress shorter or longer wavelength light than the excitation light wavelength, while passing the photoluminescence signal. For classical photoluminescence, the filter should block the excitation source wavelengths and all shorter wavelengths (long-pass filter). For up-conversion photoactive agents, the filter is selected to block excitation light and all longer wavelengths. In both cases, a narrow pass filter transparent only for photo stimulated light is desirable, especially when the stimulated light has a narrow emission band. The resulting background light suppression will provide the best effect on the photoluminescence signal contrast ratio (i.e., signal-to-background ratio).

Optical filters tuned to almost any selected cutoff, low-pass, band-stop or band-pass configuration are commercially available from suppliers such as Chroma Technology Corporation. The optical filter configuration for a given application is dictated by the available wavelengths of the selected excitation light source and by the selected ink-compatible fluorophore's absorption and photoluminescence characteristics.

The photodetector 38 may be a photo-multiplier tube or photodiode. Suitable photodetectors are commercially available from such suppliers as Hamamatsu, Vishay, Osram, Sony, Texas Advanced Optoelectronic Solutions, and others. In some applications, a single incident light source is employed, accompanied by a single in-system photoluminescence detector. In some applications, more than one illumination source and more than one photodetector may be used if desired. There is no requirement for a one-to-one pairing of illumination sources and photodetectors. The photodetector/optical filter assembly may be either fixed or movable.

It should be understood that the specific manner in which the drop detection assembly is implemented in any given printer configuration is not limited to just those illustrated in the figures. As explained in more detail below, the present photoluminescence-based devices are not dependent on source-to-detector angle and offer greater flexibility for printer integration of photoluminescence-based drop detection capabilities compared to existing scatter-reliant printers equipped for drop detection.

The present photoluminescence based drop detection approach represents an improvement over customary light scatter-based approaches to drop detection in which in-printer scattering sites regularly direct contaminating light toward the in-system detector, similar to the background contamination 84 and in-printer scattering sites 90 illustrated in FIG. 2. In scatter-based systems, despite inclusion of light absorption materials opposite the light source, and despite optimal positioning of the detector relative to the light source, there is inevitably unwanted stray scattered light that is directed back into the detector along with the desired scatter-based signal. As a result, the total contrast ratio is compromised in scatter-reliant systems, thereby imposing operational limits on the signal detectability. By "doping" black or color ink supplies with a fluorescent agent ("dopant") in small concentrations, a new signaling component is introduced into the total response. Including the dopant produces a "total response" (i.e., scattering+fluorescence). Instead of simply redirecting incident light toward the detector (i.e., scattering) the fluorescent agent generates longer wavelength light emissions that are distinct from the impinging excitation light.

To avoid background contamination in the present apparatus and methods the light that reaches the detector is filtered, for example, using a long-wavelength passing filter, as illustrated in FIG. 2. Thus, the only possible signal available for detection in the present apparatus and methods is emergent from in-flight drop and excitation light-beam interactions (photoluminescent signal). This means the only objects the detector "sees" are the in-flight drops, as desired. Doping of a black, color, or colorless inkjet ink using one or more fluorophore species improves the in-flight optical detectability of ink droplets ejected from printhead nozzles compared to scatter-based technologies. These fluorescent agents or additives offer a photoluminescent-reliant means for monitoring pen performance (contrasting scatter-based techniques), and uniquely separate the excitation light source from the wavelength band monitored by the in-system detector. This approach provides an inherently lower optical background signal and is less sensitive to system configuration specifics than light scattering approaches, thus presenting fewer avenues for signal contamination. Due to the low additive doping concentrations, the present approach also avoids color shifting and/or compromises of the typical optical density characteristics associated with many in-system inks.

Utilization of the disclosed photoluminescence-based strategy permits the viable in-flight detection of ink classes (e.g., carbon black inks) that have plagued the efficacy and performance capabilities of other optically-based nozzle health tracking technologies. For example, black ink is highly absorptive for all wavelengths and represents an extreme challenge for all kinds of illumination sources. Detectability challenges with color inks depend on the illumination light and the absorption band of the ink. Most color inks have very low absorption above about 750 nm wavelength. For those inks, an 850 nm excitation wavelength is used in most light scattering drop detection contexts. For red illumination (about 640±30 nm), cyan ink is the second most challenging to manage, after black ink, by signal strength.

Referring to FIGS. 3A-C, in some apparatus utilizing a fixed print bar design, drop detection assembly 30 may be configured to move along the side of transporter 20 and print bar 10 to scan the droplet output of individual nozzles as directed by controller 50. Within assembly 30, the photodetector 38 and long-wavelength passing filter 36 are configured to be either independently movable or stationary. There is no requirement for specific set angles between the excitation source and the detector in a photoluminescence-based drop detection system 30 because fluorescence is a spatially uniform signal, unlike light scattering. This permits greater flexibility for printer configuration development as a result of having more options for detector positioning relative to excitation light source positioning, as compared to light scatter-reliant detection equipment. Hence, a photoluminescence-based drop detection module or assembly can effectively be "squeezed" into many more printer form factors than would be possible using scatter-reliant approaches, for various in-use situations.

As illustrated in FIGS. 3A and 3C, in some instances the excitation light source 32, the photodetector 38 and the filter 36 are positioned on the same side of the print bar 10. As illustrated in FIG. 3B, for some applications, the components of assembly 30 may be separated into two sections with the excitation light source 32 located on the opposite side from the photodetector 38 and filter 36. In either case, assembly 30 is configured to move forward or backward, as indicated by the solid arrows in FIGS. 3A-C, to scan the droplets ejected from the individual nozzles, in sequence.

Figure 4:
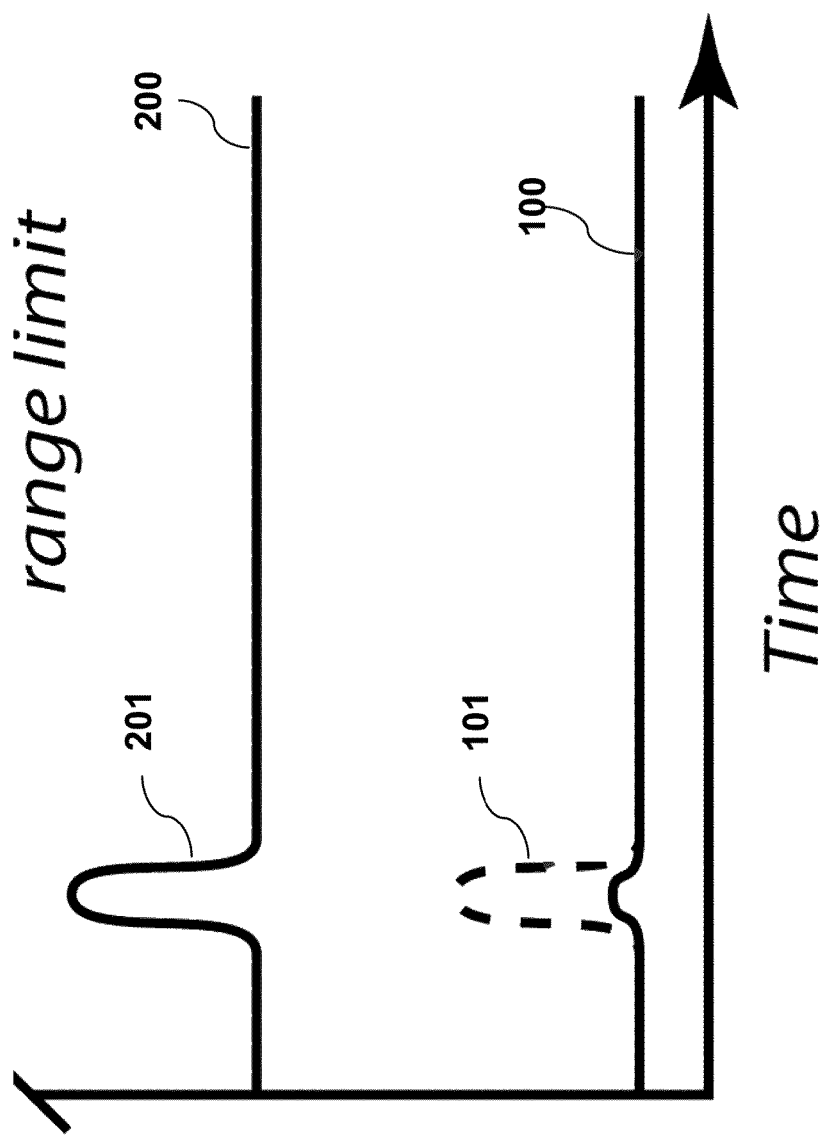
FIG. 4 is a graph comparing backscattering drop baseline and detection signals to photoluminescence drop detection baseline and detection signals.

Optical scattering techniques necessarily contend with an inherently sizeable background signal level due to the propensity for in-printer components other than the ejected drop to direct excitation light back toward the in-system detector (comparative BDD K signal 200 in FIG. 4). Such an effect contaminates the total measured signal, confounding the contrast ratio that is feasible in such systems. The addition of fluorescent additives to inkjet ink formulations, and the use of an in-system wavelength limiting filter offers a different optical strategy for monitoring drop ejection and for tracking nozzle health. Fluorescent markers operate as molecular constructs that absorb light at a prescribed excitation frequency ($v_{ex}$). The associated incident excitation energy ($hv_{ex}$) causes electrons positioned within the marker to transition from a baseline energy condition ($S_0$) to a higher energy state ($S_1$). Equation (1) describes such a process:

$$S_0 + hv_{ex} \rightarrow S_1 \quad (1)$$

Electrons naturally exhibit a preference to remain in the lowest accessible energy states as their residence within the $S_1$ energy condition is a thermodynamically unstable configuration. Eventually electrons occupying high-energy states will transition back to the $S_0$ state, and in so doing release energy through the generation of both heat and photon emissions ($hv_{em}$). The mathematical equation of this process is shown in Equation (2).

$$S_1 \rightarrow S_0 + hv_{em} + \text{heat} \quad (2)$$

In fluorescent materials, energy state structure is configured in ways that it becomes more favorable for the bulk of the released electron state transition energy to take the form of a photon emission response. Notably, the wavelength of the emitted photons are generally shifted to longer wavelengths (and thus lower frequencies) than those incident from the excitation source (i.e., $v_{ex} > v_{em}$). From the standpoint of total signal generated, the addition of small concentrations of fluorescence additives to inks causes only a miniscule amount of additional photon energy to arrive at the in-system detector. If, however, one tunes the in-printer detection system to specifically monitor only the emitted fluorescence photon energy using a long-wavelength pass filter, the nozzle health tracking apparatus can viably neglect all scattering signal components thus discarding the sizeable background contaminating light stemming from non-drop sources (as represented by cloud 90 in FIG. 2).

In FIG. 4, the fluorescence signal background 100 is much lower than that of prior light scatter drop detection (LSDD) based system 200, and the fluorescence peak 101 (enhanced by doping an ink with fluorescent agents) offers a viably detectable signal response that runs little risk of clipping against the detector's range limit. In contrast, the background (stray light) level 200 in the LSDD system is closer to the detection range limit and a signal peak 201 can easily exceed the dynamic detectibility limit of the photodetector. Thus, in a typical LSDD system, there is much less range for detecting signal strength variations. As it is normally much more challenging to generate notable fluorescent responses from non-drop sources that would be tuned to the emission wavelengths of light-stimulated drops, this photoluminescence approach greatly reduces the inherent background (stray light) levels associated with such an analysis tactic. In addition, if such non-drop stray light contamination sources happened to be endemic to a particular system, it would be feasible to readily select an alternative fluorophore with differing emission characteristics for use in the inkjet ink. A larger dynamic range is needed in systems that leverage scatter-reliant means, which can have implications for how much in-system electronic amplification is possible and the analysis speed made possible by a given detection module.

The present photoluminescence detection approach thus provides for tuning of the detector response to drop-specific characteristics. In other words, only when drops exist can a signal appear at the detector. Thus the present methods and detection apparatus configuration provide a virtually stray light contamination-free means for monitoring both black and color inks in essentially any inkjet system. The enhanced detection capability made possible by the present detection apparatus and methods, together with a suitably doped inkjet ink, offer improved nozzle condition assessment and monitoring capabilities, and new flexibilities for improved printer servicing and maintenance.

Accordingly, in some embodiments a drop detection assembly is provided which comprises (a) a printhead configured to eject ink drops comprising a fluorescent agent toward an ink drop receiver, and (b) a photoluminescence (PL) detection system. The PL detection system comprises ($b_1$) a source of excitation light configured to direct light onto an ink drop in-flight ejected from the printhead, ($b_2$) an optical filter disposed in a fluorescence emission path, and ($b_3$) a photodetector. The optical filter is configured to pass fluorescent light of a first wavelength or range of wavelengths emitted from said drop in-flight, while blocking light of a second wavelength or range of wavelengths. For example, the second wavelength or range of wavelengths which is blocked may be equal to or longer than the excitation light wavelength. The photodetector is also disposed in the fluorescence emission path, receives emitted fluorescence light passed by the optical filter, and produces an electronic signal corresponding to the received fluorescent light.

A drop detection assembly may include a controller that communicates electronically with both the printhead and the photoluminescence detection apparatus, and which is programmed to determine (based upon monitored electronic signaling) various characteristics of the in-flight ink drop. The drop detection assembly may also include an inkjet ink supply comprising a fluorescent agent, wherein the controller is, optionally, in electronic communication with the ink supply during operation of the drop detection assembly.

A printer is provided in some embodiments which comprises a printhead assembly including a printhead that ejects ink drops containing a fluorescent agent, during operation of the printer. The printer also includes a photoluminescence detection system, an optical filter and a photodetector. The photoluminescence detection system is configured to direct light onto an ink drop in-flight ejected from the printhead, during operation of the printer in drop detection mode. The optical filter is disposed in a fluorescence emission path and is configured to pass a wavelength of the emitted fluorescence and to block a wavelength of the excitation light. The photodetector is configured to receive emitted fluorescence from the drop in flight after passage through the filter, and to produce an electronic signal corresponding to the received fluorescence. The printer also includes a print media transport assembly, an ink drop receiver, and a controller that is operatively connected to the printhead assembly, photoluminescence detection system and print media transporter.

Doped Inkjet Ink

An inkjet ink formulation which lends itself to use for nozzle health analysis generally includes a liquid vehicle (e.g., water, organic solvents, co-solvents), colorant and a fluorescent agent or additive ("dopant"). Suitable ink vehicles may include, but are not limited to water, solvents and co-solvents, and may include one or more other ink components such as buffers, biocides, sequestering agents, viscosity modifiers, surfactants, humectants and dispersants.

The ink may also contain any other customary component of inkjet inks. For many applications, existing commercially available inkjet inks may be modified to include a fluorescent agent that is suitably matched to a selected excitation light source, detector and optical filter.

Fluorescent Agent.

Any suitable type of fluorescent agent may be used in an ink for drop detection, provided that its emitted fluorescence wavelength lies within the sensitivity and detection limits associated with a given detector and provided that the selected type and/or amount of fluorescent agent does not impart visible color or visible fluorescence to the ink or detrimentally affect the stability of the ink or detract from, or otherwise alter, its intended print quality. This differs from fluorescent inkjet inks (e.g., inks with colorants that fluoresce in the visible or near infrared wavelength range) which are known and commercially available. For most in-flight drop detection applications, a selected dopant must prove capable of rendering at least a 40 nm emission wavelength shift relative to the wavelength of the chosen excitation light source.

In one exemplary embodiment, a black ink contains a fluorescent agent that causes the ink to fluoresce, upon stimulation, in the visible range. This fluorescence is present to a degree that is detectable using the disclosed in-flight methodology yet, in an on-page setting, the fluorescence is masked by the strong absorption of the black ink and would not prove noticeable in normal lighting conditions. Interestingly, with proper calibration, it may prove possible to use non-human optical interrogation methods to analyze printed content and later search for the in-ink fluorescent signaling components. This capacity could serve security and/or post print-job diagnostic capabilities.

Nearly all water-soluble "dopant" fluorophores displaying high quantum yield responses (i.e., high [emitted photons]/[absorbed photons] ratios) in the optical range may potential serve as a fluorescent agent for effectively enhancing the detectability of ink drops. Those presenting large Stokes shift separations between their excitation and emission bands additionally facilitate the enhanced decoupling of drop-reliant signals from incident light, further boosting signal-to-background capabilities.

Figure 5:
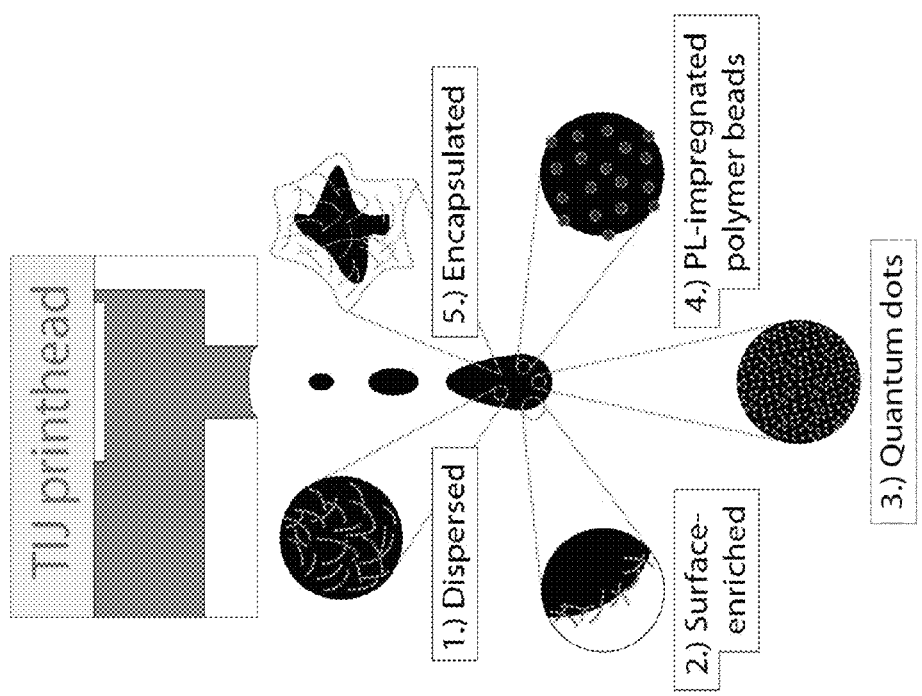
FIG. 5 schematically illustrates various types of fluorescent agents for use in photoluminescence-based drop detection, in accordance with various embodiments.
Figure 6:
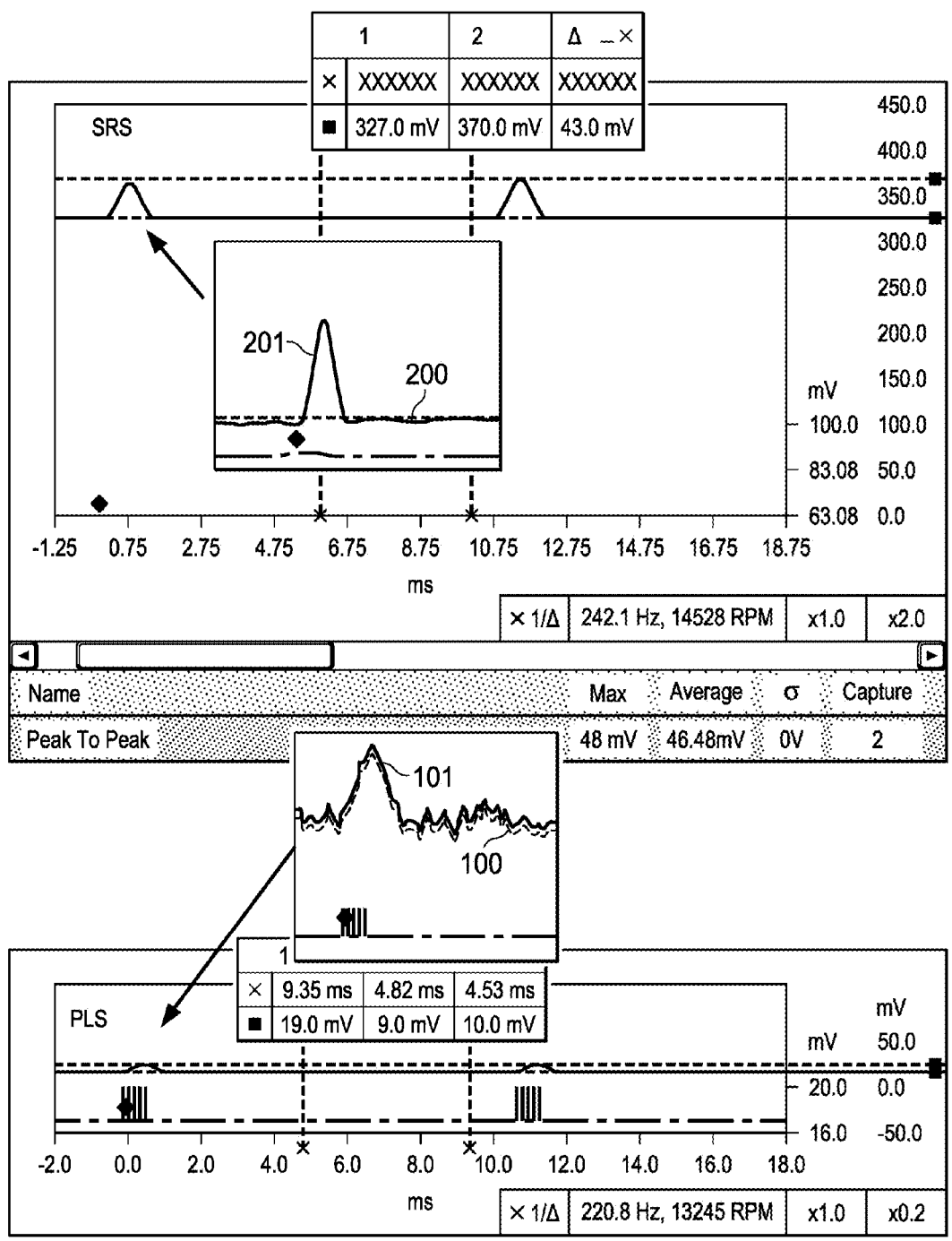
FIG. 6 is a set of raw detector signaling traces comparing in scattering-reliant signaling (SRS—top panel) to photoluminescent signaling (PLS—bottom panel) in ink vehicle with 0.01% rhodamine in accordance with one embodiment.
Figure 7:
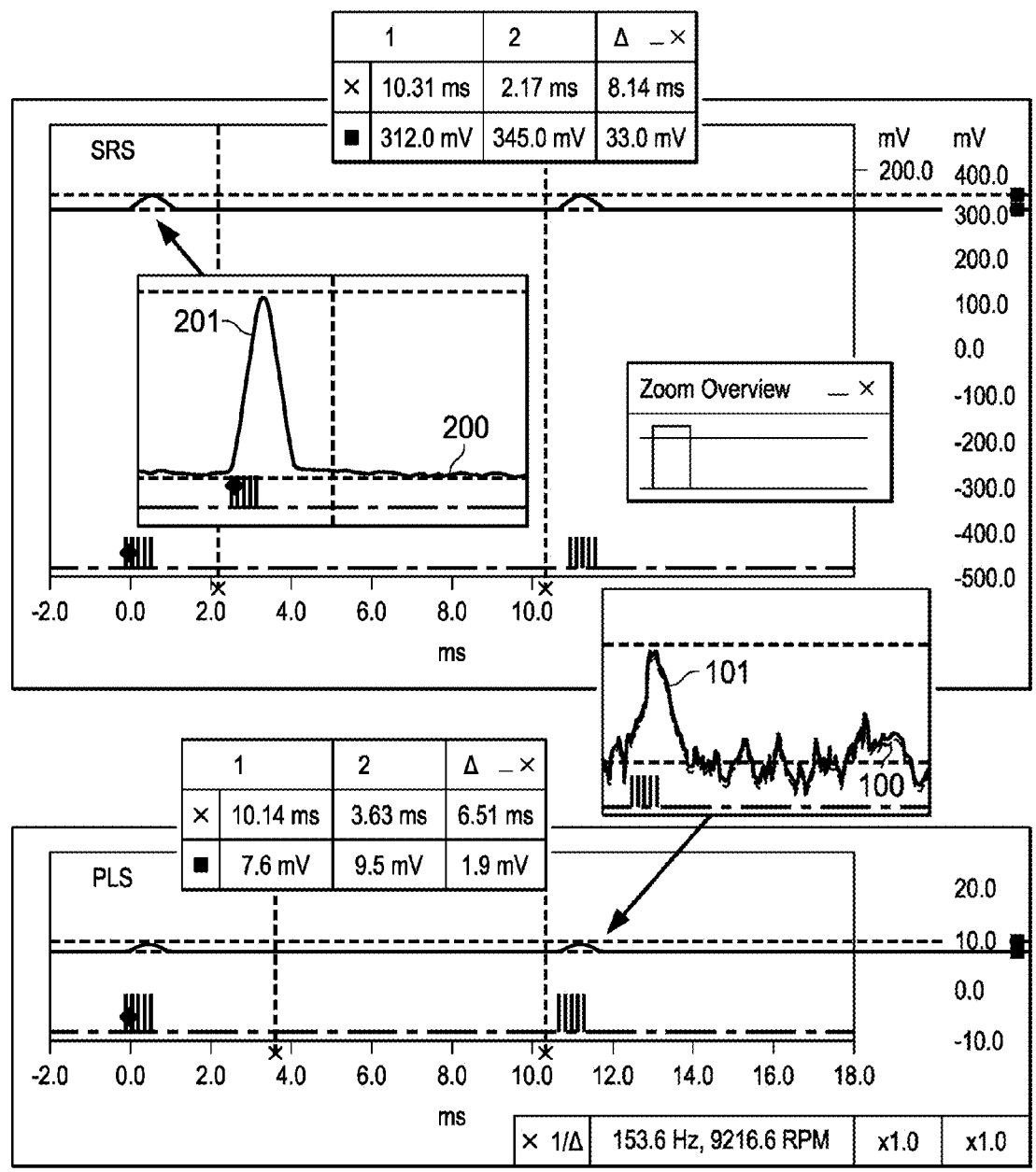
FIG. 7 is a set of raw detector signaling traces comparing in scattering-reliant signaling (top panel) to photoluminescent signaling (bottom panel) in a black ink (containing the vehicle of FIG. 6 and 0.01% rhodamine), in accordance with one embodiment.
Figure 8:
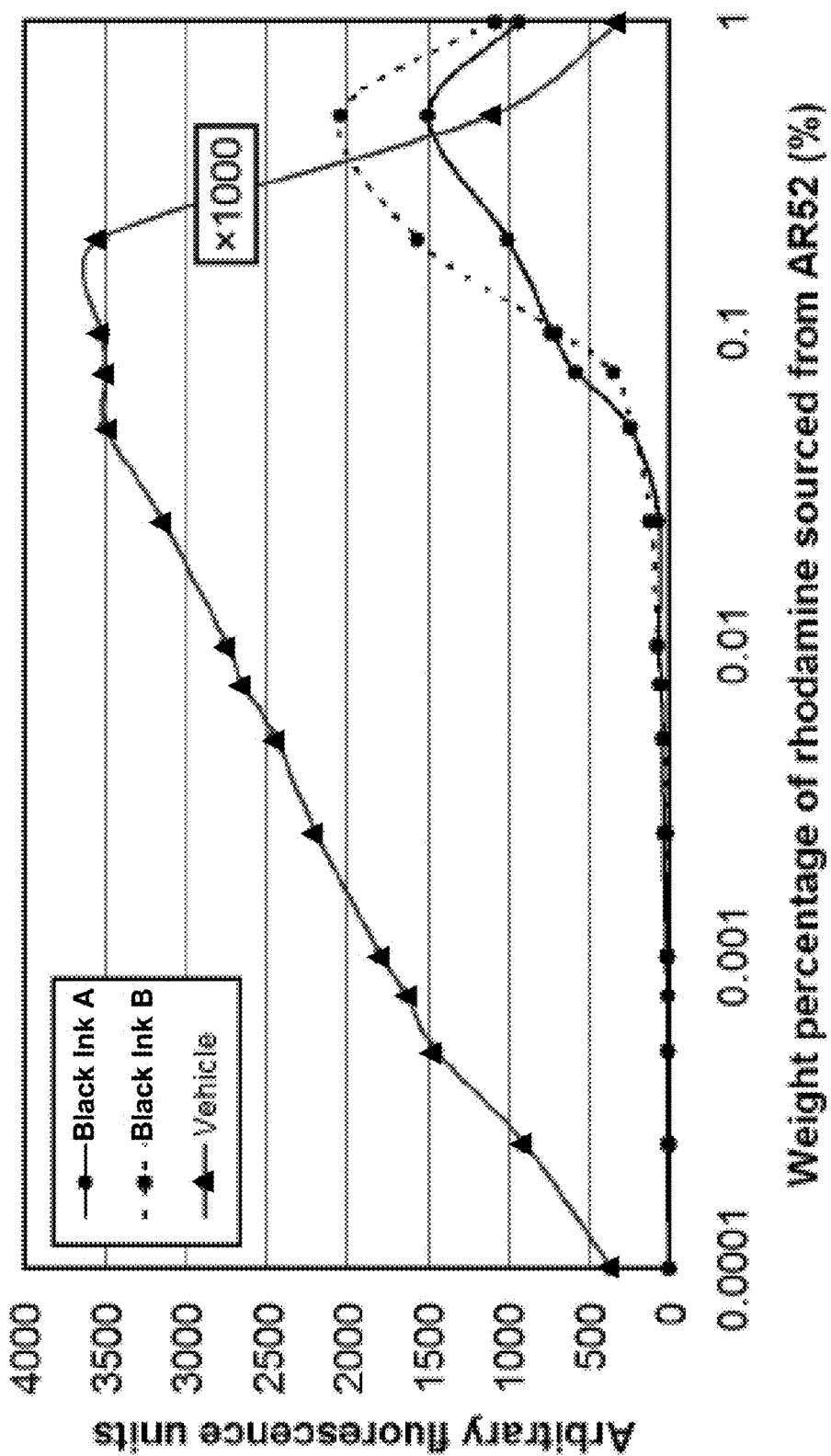
FIG. 8 is a graph showing photoluminescent response curves versus rhodamine (from AR52 stocks) weight percentage (w/w) ranging from 0.001 to 1.0 in ink vehicle, and typical varieties of black ink.
Figure 9:
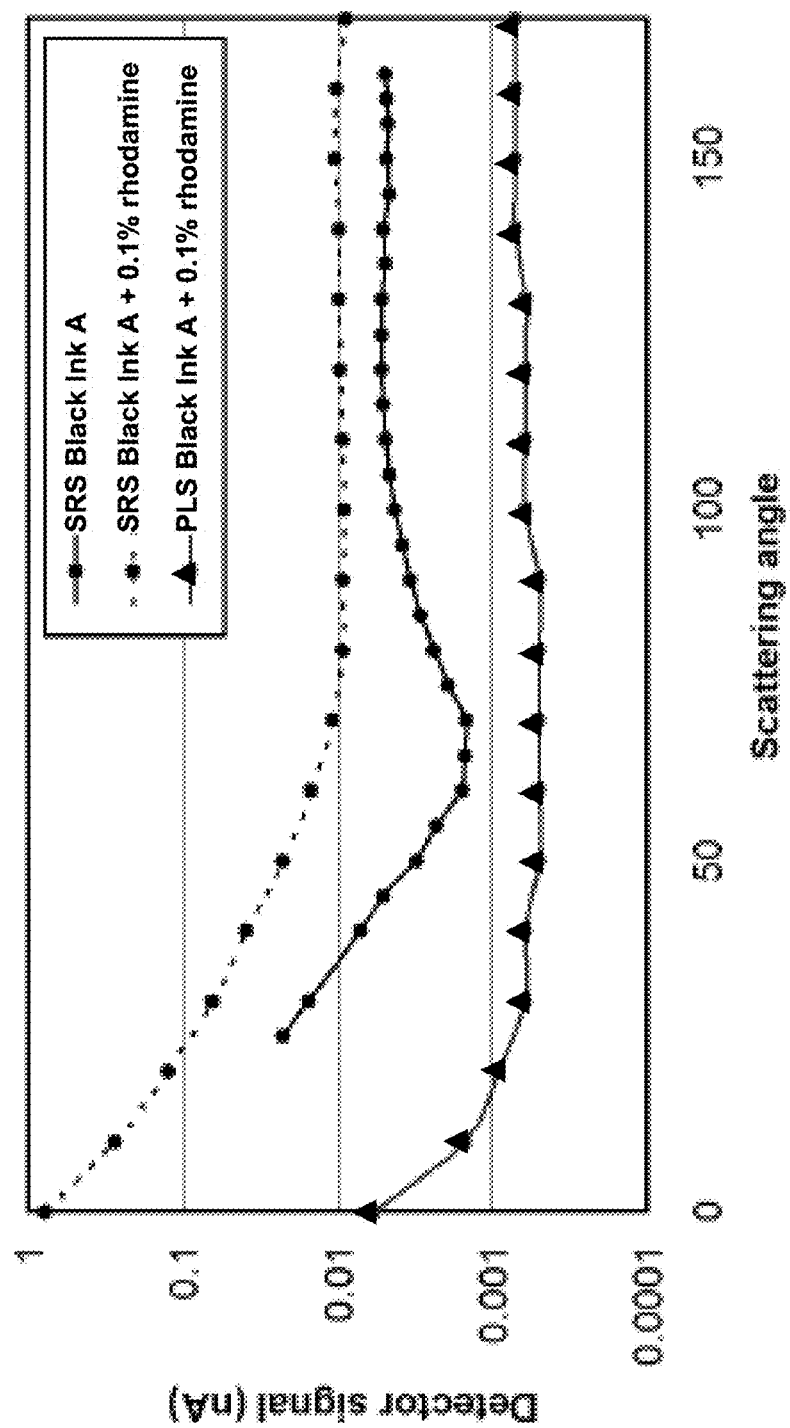
FIG. 9 is a graph showing the angular dependence of scattering reliant signaling and photoluminescent signaling in control and doped black inks detector to illumination source angles ranging from 0 to 180°.
Figure 10:
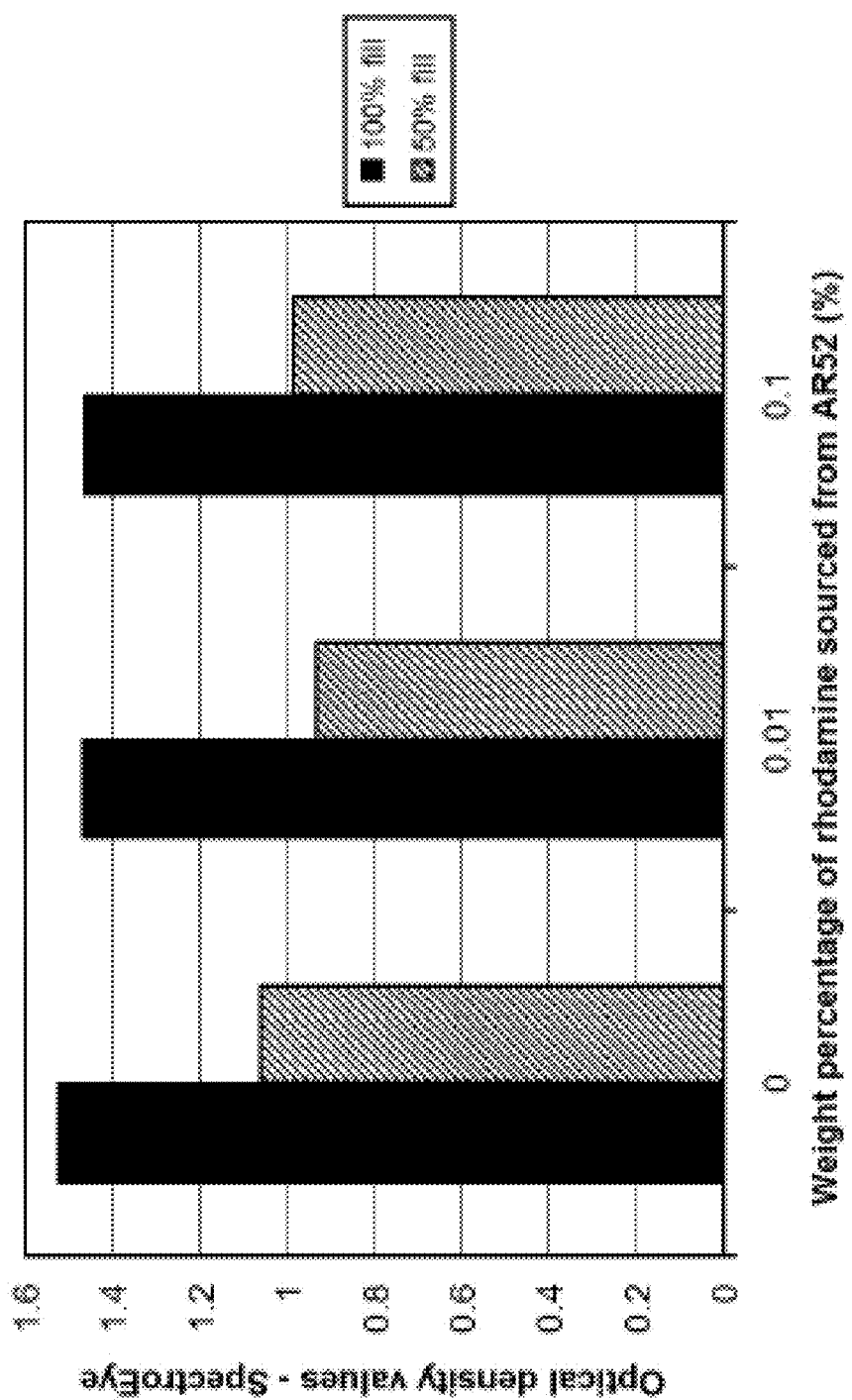
FIG. 10 is a bar graph showing black ink optical density stability over a range of dopant weight percentages, at 100% and 50% print-area fill conditions.

Various types of fluorescent agents are schematically illustrated in FIG. 5. The fluorescent agent may be a chemical compound or other material containing a fluorophore, which can be dissolved or dispersed in an ink vehicle ("Dispersed" agents 1.) in FIG. 5). In some cases, the fluorescent agent is a fluorophore coupled to an ink component that reaches a lower energy state by migrating and localizing to an outer surface of an inkjet ink drop when the drop is ejected from an inkjet nozzle ("Surface-enriched" agents 2.) in FIG. 5). For example, such ink components may be surfactants or amphiphilic molecules that contain linked combination of both hydrophilic and hydrophobic group. The surfactants can take the form of ionic, cationic, zwitterionic, and non-ionic varieties depending upon the context or needs of a particular application.

A fluorophore may be coupled to an ink component of this type using known chemical coupling/conjugation techniques, as, for example, described in Molecular Probes Handbook, A Guide to Fluorescent Probes and Labeling Technologies, Iain Johnson and Michelle T. Z. Spence, Eds., Invitrogen; Bioconjugate Techniques, G. T. Hermanson, Academic Press (1996). Quantum dots or Q-dots are another type of fluorescent agent that may be dispersed in an ink vehicle ("Quantum dots" 3.) in FIG. 5). A quantum dot strategy may either leverage commercially available Q-dots from Sigma-Aldrich, Invitrogen Corporation subsidiary of Life Technologies, Evident Technologies, Nanoco Group, or involve the targeted synthesis of other Q-dot varieties.

In some cases, the fluorescent agent is a polymer bead infused with a fluorophore that, lacking polymer containment, would prove insoluble in the ink or ink vehicle ("PL-impregnated polymer beads" 4.) in FIG. 5). The resulting fluorophore-impregnated polymer bead is then dispersed in the ink vehicle. The fluorophore may be incorporated into the polymer beads using known techniques for producing chemically impregnated polymer beads (e.g., chemical methods, physical methods, and particle sciences approaches) such as those described by Particle Sciences, Inc., Bethlehem, Pa. In some cases, the fluorescent agent is a colorant or pigment particle encapsulated in a polymeric coat ("Encapsulated" agents 5.) in FIG. 5). The polymer that forms the coat is the polymerization product of a monomer in which the fluorophore is soluble, yet the fluorophore alone is insoluble in the ink vehicle. The fluorophore-polymer encapsulated colorant particles are prepared using known techniques making polymer-encapsulated pigments, such as that described in U.S. Patent Application Publication No. 2007/0265372 entitled "Encapsulation of pigment particles by polymerization." Some non-limiting examples of fluorescent agents are rhodamine, (emits around 540 nm), fluorescein (strong emission near 220 nm and weaker emission around 475 nm), cyanine (Cy3 emits around 570 nm and Cy5 around 670 nm), Alexa Fluor (a family of dyes with emissions selectable from 442 nm to 775 nm), Calcein (emission near 515 nm), impregnated polystyrene beads (in which the most prevalent emission is within the green portion of the visible spectrum), and cadmium-free varieties of quantum dots (Q-dots) with emissions in the visible or near-infrared. All of these examples are commercially available from known suppliers.

The concentration of fluorescent agent in an ink is in the range of about 0.10 wt % to about 10 wt % of the total ink weight (w/w). In most cases, the dopant is less than 3 wt %, and for many applications is less than 1.5 wt %. For example, in many cases a dopant concentration of about 1.0 wt. % provides satisfactory drop-in-flight detection for assessment of nozzle performance (as demonstrated in the Examples below, and in FIG. 6-9). For some applications the dopant content of an ink formulation may be up to 5 wt %, 8 wt %, or even 10 wt % of the total ink weight, without rendering the optical density unacceptable, and without the dopant being visually detectable in the printed ink. In some, but not all ink formulations, the "jettability" or capability of the ink to be jetted via an inkjet nozzle declines at dopant concentrations exceeding about 5 wt %, and is generally unsatisfactory above about 10 wt %. In post-formulation analysis efforts, the loading concentration of dopant (i.e., the wt % of the ink that is dopant) may be determined by any quantitative chemical technique including, but not limited to, atomic absorption spectroscopy, IR spectroscopy, PL spectroscopy, and inductively coupled plasma optical emission spectroscopy (IC-POES).

Colorant.

Any suitable pigment- or dye-based colorant that provides acceptable optical density and print characteristics may be used to make a fluorescent agent-doped inkjet ink. For example, carbon black, graphite, vitreous carbon, charcoal, and combinations of those may serve as the colorant in some cases. In some cases, color pigments are used in formulating an inkjet ink, to provide a yellow, magenta or cyan ink, for example, or any other color in the visible spectrum, including, but not limited to red, green, light grey, etc.

In pigment-based inks, the pigment particles are typically about 5 nm to about 1 μm in diameter or longest dimension, and in some cases are about 10 nm to about 500 nm in diameter or longest dimension. Pigment particle size may be determined using any suitable light-scattering based tool for pigment particle size evaluation in dispersions. For example, one such commercially available light-scattering based device is NANOTRAC (Microtrac, Inc.). Mean particle diameter is generally volume-weighted mean particle diameter (Mv).

In most cases, the colorant pigment component comprises about 0.1 wt. % to about 6 wt. % of the ink-jet ink composition. For some applications, the pigment loading concentration is up to about 8-10 wt. % by weight of the ink. In most cases the maximum optical density of an ink is obtained at about 4-5 wt. % pigment concentration.

In still other cases, one or more black or color dye may be used instead of, or in addition to, a pigment colorant in formulating an inkjet ink. For example, combining a dye and a similarly colored pigment offers the potential advantages of both dye and pigment colorants such as lightfastness and long-term durability of many pigments, and lower cost typical of many dyes. Such combinations can often also offset decap responses that stem from pigment ink-vehicle separation (PIVS) dynamics in inks that solely rely upon pigment-based colorant strategies.

Other Components

Other components that are customarily used in inkjet ink formulations may also be included in inkjet inks used in the disclosed methods, such as water, co-solvents, buffers, surfactants, dispersants, viscosity modifiers, binders, fixatives, humectants and biocides.

Ink Drop Detection

There are many potential causes for nozzle failure in inkjet printing. In some cases, nozzles through which ink drops are ejected may become clogged with paper fibers or other debris during normal operation. A nozzle may become clogged, plugged or crusted with dry ink during prolonged idle periods. In some cases permanent failure of individual nozzles occur due to degradation of heating elements (in thermal ink jets) or by a failure in the piezoelectric crystals (in impulse printers).

An ink drop detection assembly like that illustrated schematically in FIG. 1 may be used for drop detection and to detect one or more nozzles that have failed to correctly eject drops. Drop detection and nozzle evaluation are performed either prior to or after a printing operation for fixed page wide print bars, while the printer is in drop detection mode. For scanning printheads, drop detection and nozzle evaluation may be performed before, during or after a print job, i.e., when the printhead carriage moves past the service station at the end/start of every print pass. Although media 60 is present during operation of printer 1 for printing, it is preferably absent during drop detection operations. If necessary, print bar 10 may be elevated above transporter 20 during drop detection, to provide enough space for detection assembly 30 to pass between print bar 10 and transporter 20 as it moves along the length of print bar 10, and/or to permit a longer in-flight time of ink drops.

Controller 50 is programmed to selectively energize ink ejector elements in a printhead die 16 (FIG. 2) or group of printhead dies in an appropriate sequence to eject ink from orifice or nozzle 12 toward an ink receiver 22 on, or adjacent to, transporter 20 during drop detection mode. Controller 50 is also programmed to eject ink onto print media 60 during printing mode. Controller 50 may contain information regarding structural and operational features of the printer, and is programmed to receive signals from photodetector 38, and to note a lack of signals when such signals are expected.

Controller 50 of printer 1 actuates photoluminescence detection assembly 30 and its associated carriage or other mechanism (not shown) to scan the droplet outputs of one or more nozzle 12 in sequence. Controller 50 may in some cases be programmed to skip some nozzles during a particular scanning operation if desired. Controller 50 selectively energizes ink ejector elements in a printhead die, or group of printhead dies, in print bar 10 in an appropriate sequence to eject ink drops. In drop detection operating mode, the drops are directed into an ink receptacle such as a trough 22 or spittoon in transporter 20 (FIGS. 3A-B), rather than being directed onto print media 60 as when in printing mode.

With reference to FIG. 2, excitation light source 32 which is precisely tuned to emit a collimated light beam across the flight path 70 of drops 14, the light beam being tuned to a wavelength that, when absorbed by a selected fluorescent agent additive in the ink, causes the drops in flight to emit fluorescent light having a wavelength that is longer than the wavelength of the excitation light. Various excitation light source/fluorescent emission wavelength pairings shown in Table 1 are available for drop detection using black inks, color inks and colorless inks.

TABLE 1

| Type of Ink | Excitation Wavelength Range | Emission Wavelength Range |
| --- | --- | --- |
| Black | UV | UV |
|  | UV | Visible |
|  | UV | NIR/IR |
|  | Visible | Visible |
|  | Visible | NIR/IR |
|  | NIR/IR | NIR/IR |
| Color and colorless (excluding carbon black-based) | UV | UV |
|  | UV | NIR/IR |
|  | NIR/IR | NIR/IR |

Drop detection assembly 30 scans the droplet outputs from nozzles in sequence, and the resulting fluorescent emissions from each drop form a detection path 80, as illustrated in FIG. 2. To avoid signal contamination due to stray scattered light 84 that enters the fluorescence detection path 80, the light that reaches the photodetector 38 is filtered by long-wavelength passing filter 36. The longer wavelength light (signal 82) passes through filter 36 and strikes photodetector 38, while stray, background contamination light 84, having shorter wavelengths than the emitted fluorescent light, is blocked. In this way, the drop response is separated from background contaminating sources. As a result, the detectability of fired drops is enhanced and a pure photoluminescent response from a fluorescent additive or agent is obtained.

The photodetector 38 detects the filtered light in its various intensities. The photodetector reacts to the filtered light (signal 82) by producing a corresponding current, which is subsequently amplified by, typically, a high-gain transimpedance amplifier. Signaling information can also be much more complex than just intensity alone. In addition to signal intensity or amplitude, there are other signaling components such as duration, spectral content, signal rise and fall times, peak amplitude, pulse width, and other components, that can participate in providing information that reflect drop characteristics such as size, position, and speed. The resulting electronic signals are sampled and processed to determine properties or characteristics of the respective ink drops. Based on the various signaling components detected, the controller determines ink drop characteristics such as the presence and/or absence of ink drops, the size, position and speed of the drops, and the ejection angle of the ink drops.

In accordance with some embodiments, a drop detection method is provided which comprises (a) ejecting an ink drop that includes a fluorescent agent, (b) illuminating the ink drop in flight with excitation light to excite the fluorescent agent, (c) detecting fluorescence emitted by the drop in-flight having a longer wavelength than a wavelength of the excitation light, and (d) prior to such detecting, filtering out light having a shorter wavelength than the fluorescent wavelength. In some embodiments, such ejecting comprises jetting a series of ink drops toward a drop receiver. In some cases the emitted fluorescence has a wavelength 40 nm, or more, greater than the wavelength of the excitation light. In some embodiments a disclosed method comprises converting detected fluorescence to a corresponding electrical signal and determining a characteristic of an ink drop based upon the electrical signal. In some embodiments an operational condition of an inkjet nozzle is determined based on characteristics of one or more ejected ink drops.

In some embodiments of a disclosed method, the ink drop comprises a carbon black colorant and the excitation light wavelength is in the ultraviolet, visible, near-infrared or infrared range, and the emitted fluorescence has a wavelength in the ultraviolet, visible, near-infrared or infrared range that is longer than a wavelength of the excitation light.

In some embodiments of a disclosed method, the ink drop comprises a colorant exclusive of carbon black, the excitation light wavelength is in the ultraviolet, near infrared or infrared range, and the emitted fluorescence has a wavelength in the ultraviolet, near infrared or infrared range that is longer than that of the excitation light and excluded from the visible band.

In some embodiments of a disclosed drop detection method, the ejecting comprises ejecting a plurality of ink drops from a plurality of respective nozzles, and the illuminating and detecting comprise sequentially scanning the ink drops ejected from the respective nozzles.

In some embodiments of a disclosed drop detection method, the method further comprises ejecting black ink drops containing the fluorescent agent onto a print media, to form a printed image having a KOD equal to or varying by no more than ±15% of the KOD of a printed image formed from the same black ink drops lacking said fluorescent agent.

In some embodiments, a disclosed drop detection method, further comprises ejecting black ink drops containing the fluorescent agent onto a print media, to form a printed image having a human detectable print output quality like that of a printed image formed from the same black ink drops lacking said fluorescent agent. In some embodiments of a disclosed drop detection method, the fluorescent agent comprises a chemical containing a fluorophore, quantum dots, polymer beads infused with a fluorophore, fluorophore-coupled ink components, or a fluorophore-polymer encapsulated colorant particle.

Assessment of Nozzle Condition

For some applications, controller 50 may also be programmed to determine a state or condition of particular printhead orifices or nozzles based on the above-described measured characteristics of ink drops-in-flight. Such characteristics may include, but are not limited to, ink drops that are absent where they should be present, the size and/or shape of ink drops, drop volumes, drop weights, ability to maintain a predetermined ink drop stream direction (i.e., the ability to avoid misdirecting its ink drop stream), or to determine a nozzle's ability to fire an ink drop stream at a reproducible velocity, e.g., with a velocity that does not deviate by more than ±10%. For many applications, measured characteristics include drop weights or volumes that do not deviate by more than ±10%. Still other types of measurements that may be performed include assessing whether drops on the page are colored as they are intended, for example, some drops are not enriched in color, are depleted in color, or are missing altogether.

Characteristics of the ejected ink drops-in-flight are used to assess the state or "health" of printhead structures and to evaluate selected operational features of the printer. For example, detecting that ink drops are absent where they should be present and detecting the number, size and/or shape of ink drops is used in some cases to determine whether orifices or nozzles through which ink drops are ejected, or are supposed to be ejected, are partially or fully clogged. For instance, the absence of an ink drop may indicate that a nozzle failed to fire or is misfiring. The presence of an ink drop may indicate that the nozzle is firing. The size of the ink drop provides further information pertaining to the working status of the nozzle. An ink drop that is smaller than usual indicates that a particular nozzle may be partially clogged or misfiring. The location of an ink drop may also provide further information. An ink drop that is in an unusual position or offset may suggest that the nozzle is partially blocked or clogged in some manner, rendering a misdirected drop as it leaves the orifice plate.

As another example, inkjet nozzle performance may be assessed to determine the ability of a specific print nozzle to maintain a predetermined ink drop stream direction (i.e., the ability to avoid misdirecting its ink drop stream), or to determine a nozzle's ability to fire an ink drop stream at a reproducible velocity. In some applications, a complete mapping of the health status of all nozzles on a print head is performed prior to the start of a printing job. Stemming from such signal analyses and diagnostics, a suitably programmed controller 50 may redirect the function of a defective nozzle to another compensatory nozzle in some cases. Signal analysis may determine whether a printhead requires cleaning or servicing, for example. Signal analysis may even be used for calibrating a nozzle position relative to other parts of a printer.

The disclosed equipment and methods potentially offset some of the challenges associated with obtaining reliable nozzle health diagnostics across all on-die slots, when compared to other available strategies. For example, the manner of handling background/stray light in extremely constrained drop detection space in page wide array printers, as described herein, offers advantages for increasing reliability of nozzle health detection. As the disclosed methods require only small quantities of a fluorescent agent (e.g., 0.10% to about 10% (w/w)), some of the customary additive-driven compromises in on-page ink optical densities (as measured in print samples) may also be avoided. Likewise, background contamination of the detected signal (stemming from the illumination source) and the resultant compromise in contrast ratios are reduced or eliminated by the presently disclosed methods. In many cases, a substantial improvement in the contrast ratio measured for black inks is obtainable (e.g., 10×), compared to scatter-reliant drop detection/monitoring strategies.

An additional benefit of some embodiments of the disclosed methods is that the fluorescent agent-doped ink may also be used for ink detection in printed products. In such contexts, page-scanners that monitor key emission spectra could observe on-page print characteristics that would not be visible to the naked eye for security-enabled printing, as an example.

EXAMPLES

In surveys of representative printed samples of inkjet inks doped with fluorescent agents, the optical densities native to black inks were advantageously retained, as described below. Improved detectability for in-flight drop monitoring without introducing unwanted color-shifts in printed artwork was noted in tests of representative samples of inks doped with fluorescent agents (i.e., the fluorescent agents are non-obtrusive on paper). Although additives with absorption and emission bands located within the visible wavelength range would likely introduce color shifts in cyan, magenta and yellow ink varieties, in some cases one can use a fluorescent agent that exchanges energies in near infrared (NIR) and/or infrared (IR) regions of the electromagnetic spectrum, and thus would not affect an ink's color characteristics. Such fluorescent agents may permit the use of dopant concentrations beyond even those presently demonstrated in black inks, as their addition would only be limited by ink stability and jettability concerns and not by printed sample color shifting constraints.

Example 1

Ink vehicle-based surveys were performed on vehicles "doped" with rhodamine concentrations of 0.01% (w/w) derived from acid red AR52 sources ("AR52"). Ink-vehicles "doped" with fluorescent additives but lacking the colorants associated with deployed ink varieties (a fluid type that is readily observed via in-flight optical methods) were examined by comparing the affiliate drop detection signaling seen when using 1: a scattering-based apparatus configuration ("SRS") that lacks in-system optical filtering (i.e., detecting the same wavelength as is used to excite in-flight drops), or 2: a fluorescence-based apparatus ("PLS") configuration that uses optical filtering to segregate excitation wavelengths from emission wavelengths emergent from drop interactions with the incident light source. In FIG. 6, top panel, SRS signal (201):background (200) ratio (contrast ratio) was 0.116. In the bottom panel of FIG. 6, PLS signal (101):background (contrast ratio) (100) was 1.111. Comparing these raw detector signaling traces from SRS and PLS, an order of magnitude (approximately 10×) improvement in contrast ratio readings of the PLS samples was demonstrated compared to a customary scatter-reliant method ("SRS"). This response demonstrates the power of fluorescence-based drop detection configurations over traditional scatter-reliant approaches, highlighting the capacity for reducing the overall background level in the recorded signal.

Example 2

In carbon black based inks, a complimentary set of raw detector signals were gathered (using rhodamine dopant concentrations of 0.1%), again surveying responses using both scatter-reliant means and fluorescence-based methods, as described in Example 1. The results are shown in FIG. 7. In the top panel, SRS signal (201):background (200) ratio (contrast ratio) was 0.096. In the bottom panel, PLS signal (101): background (100) (contrast ratio) was 0.200. Comparing these raw detector signaling traces from SRS and PLS, an approximately two-fold improvement in contrast readings of the PLS samples was demonstrated compared to the customary scatter-reliant method ("SRS"). This response demonstrates the power of fluorescence-based drop detection configurations over traditional scatter-reliant approaches with carbon black based inkjet ink, the class most difficult to detect via optical means. This highlights the capacity for reducing the overall background level in the recorded signal from carbon black-based inks.

Example 3

In a follow-on survey, representative carbon black-based inks were "doped" with rhodamine (reported in w/w percentages—see FIG. 8), again sourced from AR52 stocks, in varying concentrations. Black Ink A was the same carbon black-based ink as examined in Example 2, Black Ink B was a different carbon black-based ink, and the vehicle was the same as that used in Example 1. This concentration-variant survey measured photoluminescent emission signal output using a 96-well plate and vehicles/inks doped using an automated picoliter drop volume dispense tool. As the data collected in Examples 1 and 2 leveraged a dopant concentration much lower than the values that produce peak signaling (as shown in FIG. 8), the original datasets from Examples 1 and 2 were not optimized and, as such, there is ample room available for further enhancing the signal-to-background readings when our in-flight fluorescence-based drop detection method is used. In ink vehicle alone (triangles) a strong photoluminescence (PL) signal peaking near 0.1% (w/w) rhodamine is observed. Although a weaker response occurs in K ink varieties (Black Ink A and Black Ink B), additive loadings tied to peak PL responses are higher (just under 1%) than in vehicle alone due to incident light penetration depth limitations and the relevance of surface concentration conditions on ejected drops.

Example 4

Another key benefit of the present photoluminescence-based strategies, compared to scattering-reliant signaling, which was demonstrated with the carbon black-based ink of Example 2, is a lack of angular dependence in the measured signal detector responses. A graph of measured detector signal intensity versus scattering angle is shown in FIG. 9. Regardless of the angle between the excitation light source and the in-system photodetector, the fluorescence-based methods ("PLS") showed a markedly flatter and more uniform response than the typical scatter-based means ("SRS"). Thus, the available configuration capabilities for implementing PLS detection system designs are greatly enlarged compared to scatter-reliant designs, as the excitation light source and the detection device can now be positioned in virtually any position relative to one another in a photoluminescence-based system.

Example 5

The optical density stability of the carbon black-based ink of Example 2 was examined over rhodamine dopant concentrations ranging from 0 to 0.1% (w/w), sourced from AR52 stocks. The printed inks were examined from a prints-on-page perspective with both 50% and 100% area fills. As the bar graph presented in FIG. 10 shows, at each fill level surveyed, the optical densities of the rhodamine-doped inks did not vary from the control sample by more than about −3% to about −12%. None of the additive concentrations examined in these studies dramatically compromised the nominally high optical density characteristics of the baseline inks and color shifting was not apparent. As shown in FIG. 10, photoluminescence agent loading levels capable of producing in-flight optically detectable drop signals can avoid significantly impacting native optical density values for printed K inks.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A drop detection method, comprising:
ejecting an ink drop from a nozzle, the ink drop including a fluorescent agent;
illuminating the ink drop in-flight with light having a first wavelength range to excite the fluorescent agent and to cause emission of emitted light having a second wavelength range from the ink drop, the second wavelength range being longer than the first wavelength range, the second wavelength range including fluorescent light due to the ink drop including the fluorescent agent, the ink drop being illuminated in-flight to enable a condition of the nozzle to be determined;
filtering light from the ink drop to remove the first wavelength range; and
detecting the light emitted from the ink drop in-flight and having the second wavelength.

2. The method of claim 1, wherein the ejecting includes jetting a series of ink drops toward a drop receptacle.

3. The method of claim 1, wherein the second wavelength range is at least 40 nm longer than the first wavelength range.

4. The method of claim 1, wherein the nozzle is one of a plurality of nozzles and the ink drop is one of a plurality of ink drops, the ejecting includes ejecting the ink drops from the respective nozzles, and the illuminating and detecting include sequentially scanning for the second wavelength range from the ink drops in-flight.

5. The method of claim 1, wherein the ink includes a carbon black colorant, the first wavelength range is in an ultraviolet, visible, near-infrared or infrared range, and the second wavelength range is in the ultraviolet, visible, near-infrared or infrared range.

6. The method of claim 1, wherein the ink drop includes a colorant exclusive of carbon black colorant, the first wavelength range is outside of a visible band, and the second wavelength range is in the ultraviolet, near infrared or infrared range.

7. The method of claim 1, further including ejecting first black ink drops containing the fluorescent agent onto a print media to form a printed image having a black optical density equal to or varying by no more than ±15% of the black optical density of a printed image formed from second black ink drops, the second black ink drops having substantially the same composition as the first black ink drops but lacking fluorescent agent included in the first black ink drops.

8. The method of claim 1, further including ejecting first black ink drops containing the fluorescent agent onto a print media to form a printed image having a human detectable print output quality similar to a printed image formed from second black ink drops, the second black ink drops having substantially a same composition as the first black ink drops but lacking the fluorescent agent.

9. The method of claim 1, wherein the fluorescent agent includes at least one of fluorophore, quantum dots, polymer beads infused with a fluorophore, or fluorophore-polymer encapsulated colorant particles.

10. The method of claim 1, further including determining a characteristic of the ink drop based on the light emitted from the ink drop.

11. The method of claim 10, further including determining the condition of the nozzle based on the characteristic of the ink drop.

12. The drop detection method of claim 1, wherein the ink component is a surfactant, or an amphiphilic molecule.

13. The drop detection method of claim 12, wherein the fluorescent agent is coupled to the surfactant or to the amphiphilic molecule.

14. A drop detection assembly, comprising:
a printhead to eject an ink drop including a fluorescent agent toward an ink drop receiver; and
a photoluminescence detection system, including:
a light source to direct first light exhibiting a first wavelength range onto the ink drop in-flight, second light exhibiting a second wavelength range to be emitted from the ink drop due to the fluorescent agent in response to the first light passing through the ink drop in-flight, the second wavelength range including at least one wavelength corresponding to fluorescent light;
an optical filter disposed in a path of the second light, the optical filter to pass the at least one wavelength of the second light corresponding to the fluorescent light, the optical filter to block light of the first wavelength range from passing through the optical filter; and
a photodetector disposed in the path of the second light, the optical filter disposed between the light source and the photodetector, the photodetector to receive the at least one wavelength of the second light corresponding to the fluorescent light that passes through the optical filter, the photodetector to produce a signal corresponding to the at least one wavelength of the second light received from the ink drop in-flight, the signal to be used to determine a condition of the printhead.

15. The drop detection assembly of claim 14, further including a controller in electronic communication with the printhead and the photodetector, in response to the signal, the controller to determine a characteristic of the ink drop.

16. The drop detection assembly of claim 14, further including an inkjet ink supply including the fluorescent agent.

17. The drop detection assembly of claim 14, wherein a position of the light source and a position of the sensor are angle independent.

18. A printer comprising:
a printhead assembly including a printhead to eject an ink drop containing a fluorescent agent;
a light source to direct first light of a first wavelength range onto the ink drop in-flight, second light of a second wavelength range to be emitted from the ink drop when the first light passes through the ink drop in-flight, the second wavelength range including at least one wavelength corresponding to fluorescent light;
an optical filter disposed in a path of the second light, the optical filter to pass fluorescent light of the second wavelength range, and to block fluorescent light of the first wavelength range; and
a sensor to receive the fluorescent light passed through the optical filter, the sensor to produce a signal in response to the fluorescent light received via the optical filter;
a print media transport assembly;
an ink drop receiver; and
a controller to determine a condition of the printhead in response to the signal from the sensor.

19. The printer of claim 18, wherein an angle between the light source and the sensor is not fixed.

* * * * *